United States Patent [19]

Yao

[11] Patent Number: 5,468,147
[45] Date of Patent: Nov. 21, 1995

[54] ORTHODONTIC WIRE

[76] Inventor: Stephen C. Yao, 2075 Sutter St., #503, San Francisco, Calif. 94115

[21] Appl. No.: 278,098

[22] Filed: Jul. 21, 1994

[51] Int. Cl.⁶ .................................................. A61C 3/00
[52] U.S. Cl. ............................................................ 433/20
[58] Field of Search ................................................ 433/20

[56] References Cited

U.S. PATENT DOCUMENTS

| | | | |
|---|---|---|---|
| 4,659,310 | 4/1987 | Kotteman | 433/20 |
| 4,850,865 | 7/1989 | Napolitano | 433/20 |
| 4,897,036 | 1/1990 | Kesling | 433/20 |
| 5,174,753 | 12/1992 | Wool | 433/20 |
| 5,271,733 | 12/1993 | Chikami et al. | 433/20 |

*Primary Examiner*—Cary E. O'Connor

[57] ABSTRACT

An orthodontic wire for applying torque forces to a patient's teeth. The inventive device includes a wire having a substantially rectangular cross section with longitudinal grooves extending along exterior surfaces of the wire. The wire is more flexible than standard square or rectangular wires, yet still retains the ability to apply a torquing force absent in round wire.

3 Claims, 2 Drawing Sheets

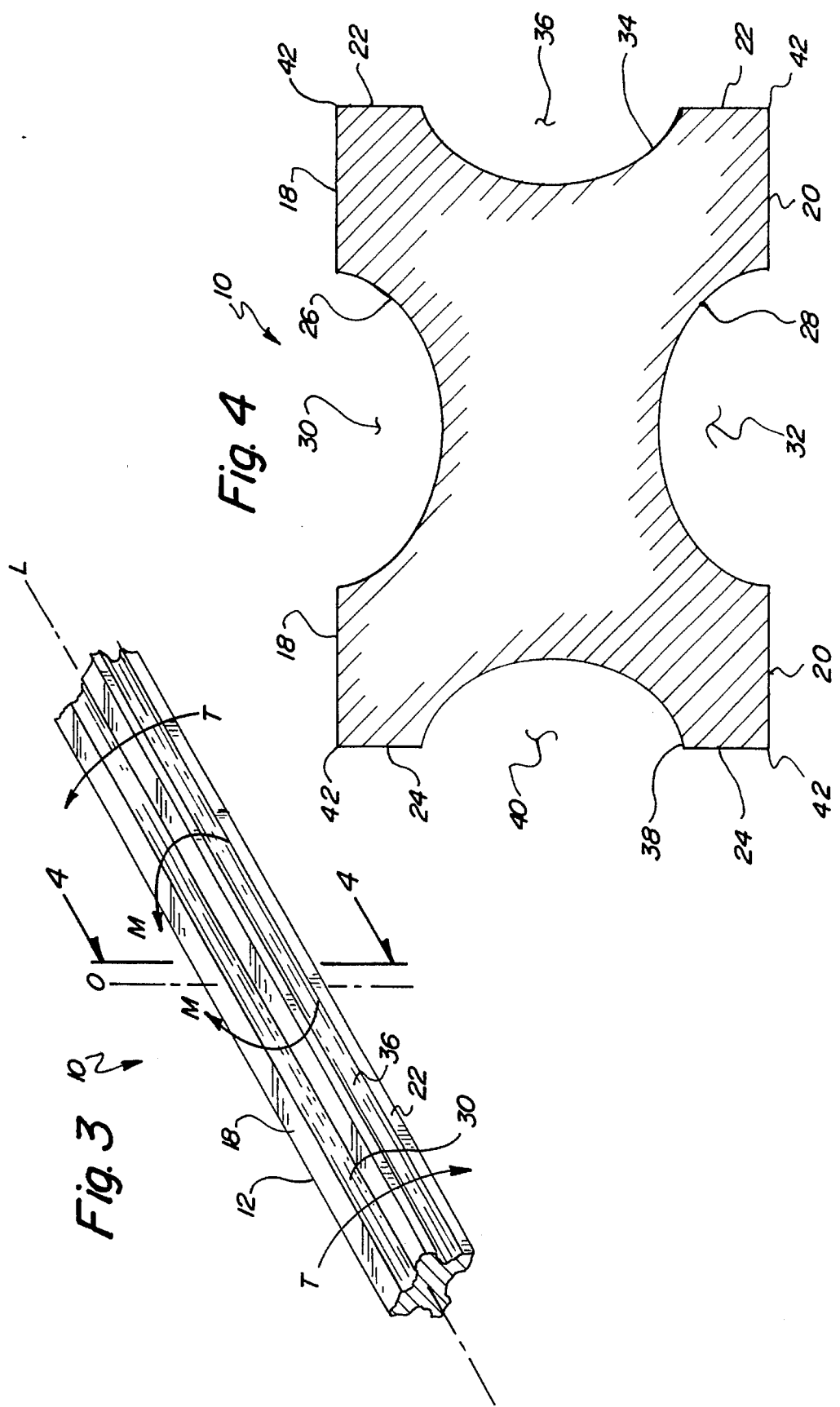

ORTHODONTIC WIRE

BACKGROUND OF THE INVENTION

1. Field of the Invention

The present invention relates to dental devices and more particularly pertains to an orthodontic wire for applying torque forces to a patients teeth.

2. Description of the Prior Art

The use of dental devices is known in the prior art. More specifically, dental devices heretofore devised and utilized are known to consist basically of familiar, expected and obvious structural configurations, notwithstanding the myriad of designs encompassed by the crowded prior art which have been developed for the fulfillment of countless objectives and requirements.

In orthodontics, wires of different sizes are used to perform different functions and to move teeth within a patient's mouth. Prior art wires include round cross-section wires, and square or rectangular cross-section wires. Rectangular wires having the advantage of providing twisting or torquing capability which may be imparted to the patient's teeth. However, such rectangular or square wires are difficult to bend and form into the specific contour needed for an individual patient's mouth. Round wires, however, are more flexible than square or rectangular wires and are more easily conformed to the patient's mouth. Thus, round wires are more likely to be used in situations requiring more flexibility of the wire. A disadvantage of round wires is their inability to apply twisting or torquing forces to the patient's teeth.

Examples of known prior art dental devices include U.S. Pat. No. 5,174,753; U.S. Pat. No. 5,063,082; U.S. Pat. No. 4,892,479; U.S. Pat. No. 4,869,666; and U.S. Pat. No. 3,729,824.

While these devices fulfill their respective, particular objectives and requirements, the aforementioned patents do not disclose an orthodontic wire for applying torque forces to a patient's teeth which includes a wire having a substantially rectangular cross-section with longitudinal grooves extending along exterior surfaces of the wire.

In these respects, the orthodontic wire according to the present invention substantially departs from the conventional concepts and designs of the prior art, and in so doing provides an apparatus primarily developed for the purpose of applying torque forces to a patient's teeth.

SUMMARY OF THE INVENTION

In view of the foregoing disadvantages inherent in the known types of dental devices now present in the prior art, the present invention provides a new orthodontic wire construction wherein the same can be utilized for applying torque forces to a patient's teeth. As such, the general purpose of the present invention, which will be described subsequently in greater detail, is to provide a new orthodontic wire apparatus and method which has many of the advantages of the dental devices mentioned heretofore and many novel features that result in a orthodontic wire which is not anticipated, rendered obvious, suggested, or even implied by any of the prior art dental devices, either alone or in any combination thereof.

To attain this, the present invention generally comprises an orthodontic wire for applying torque forces to a patient's teeth. The inventive device includes a wire having a substantially rectangular cross section with longitudinal grooves extending along exterior surfaces of the wire. The wire is more flexible than standard square or rectangular wires, yet still retains the ability to apply a torquing force absent in round wire.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new orthodontic wire apparatus and method which has many of the advantages of the dental devices mentioned heretofore and many novel features that result in a orthodontic wire which is not anticipated, rendered obvious, suggested, or even implied by any of the prior art dental devices, either alone or in any combination thereof.

It is another object of the present invention to provide a new orthodontic wire which may be easily and efficiently manufactured and marketed.

It is a further object of the present invention to provide a new orthodontic wire which is of a durable and reliable construction.

An even further object of the present invention is to provide a new orthodontic wire which is susceptible of a low cost of manufacture with regard to both materials and labor, and which accordingly is then susceptible of low prices of sale to the consuming public, thereby making such orthodontic wires economically available to the buying public.

Still yet another object of the present invention is to provide a new orthodontic wire which provides in the apparatuses and methods of the prior art some of the advantages thereof, while simultaneously overcoming some of the disadvantages normally associated therewith.

Still another object of the present invention is to provide a new orthodontic wire for applying torque forces to a patient's teeth.

Yet another object of the present invention is to provide a new orthodontic wire which includes a wire having a substantially rectangular cross-section with longitudinal grooves extending along exterior surfaces of the wire.

Even still another object of the present invention is to provide a new orthodontic wire which is more flexible than standard square or rectangular wires, yet still retains the ability to apply a torquing force absent in round wires.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an isometric illustration of a length of the wire.

FIG. 4 is a cross sectional view taken along line 4—4 of FIG. 3.

DESCRIPTION OF THE PREFERRED EMBODIMENT

Figure 1:
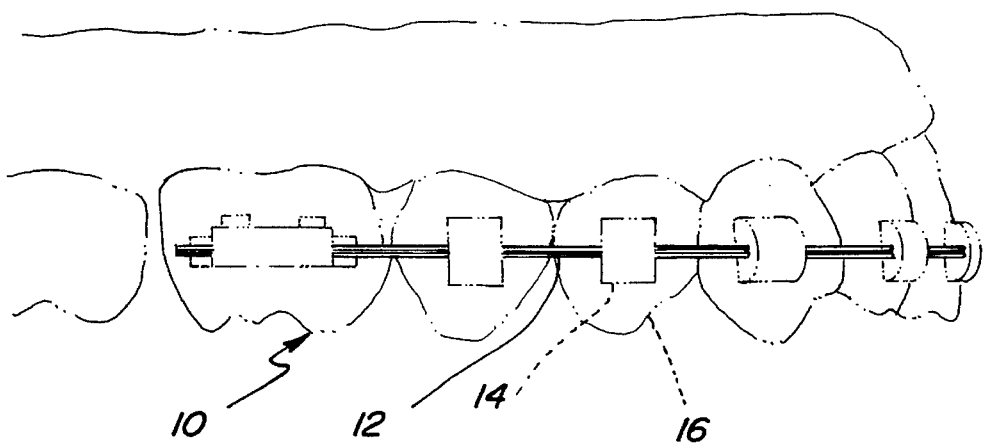
FIG. 1 is a side elevation view of an orthodontic wire according to the present invention as installed along a patient's teeth.
Figure 2:
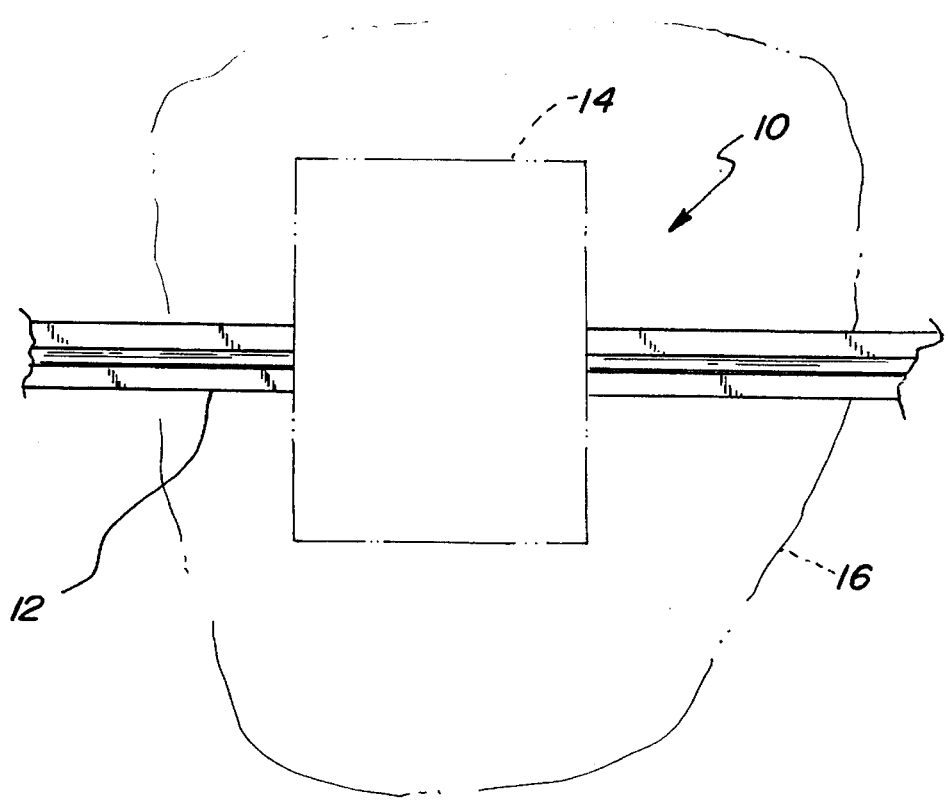
FIG. 2 is an enlarged side elevation view of the installed orthodontic wire.

With reference now to the drawings, and in particular to FIGS. 1–4 thereof, a new orthodontic wire embodying the principles and concepts of the present invention and generally designated by the reference numeral 10 will be described.

More specifically, it will be noted that the orthodontic wire 10 comprises a length of wire 12 which can be utilized in the construction of the orthodontics structure illustrated in FIG. 1, wherein the wire 12 extends through a tooth bracket 14 secured to an individual tooth 16 within a patient's mouth. The tooth bracket 14 is of conventional construction and is secured to the tooth in a conventional manner by the use of adhesives or the like. The tooth bracket 14 preferably includes an unlabelled through-extending aperture having a rectangular cross-section closely matching the rectangular cross-section of the wire 12. Referring now to FIGS. 3 and 4, it can be shown that the wire preferably has a rectangular cross-section, as illustrated in FIG. 4, and includes an upper surface 18 spaced from and parallel to a lower surface 20, and an outer surface 22 spaced from and parallel to an inner surface 24. The upper and lower surfaces 18, 20 are oriented at orthogonal angles relative to the outer and inner surfaces 20, 22 to define the substantially rectangular cross-sectional shape illustrated in FIG. 4. Preferably, the upper surface 18 and the lower surface 20 are of a first transverse dimensional length, and the outer surface 22 and the inner surface 24 are of a second transverse dimensional length, wherein the first transverse dimensional length is substantially greater than the second transverse dimensional length. Alternatively, the first transverse dimensional length may be substantially equal to the second transverse dimensional length so as to define a substantially square cross-section wire 12.

Preferably, the wire 12 is symmetrically oriented about a longitudinal axis "L" as shown in FIG. 3. The wire 12 further includes an upper longitudinal cutout 26 extending along a length of the wire 12 and parallel to the longitudinal axis "L", as well as a lower longitudinal cutout 28 extending along the wire in a substantially similar orientation along the lower surface 20. The upper longitudinal cutout 26 defines an upper longitudinal groove 30, and the lower longitudinal cutout 28 defines a lower longitudinal groove 32. Further, the outer surface 22 includes an outer longitudinal cutout 34 extending along the length of the wire 12 to define an outer longitudinal groove 36. Similarly, an inner longitudinal cutout 38 extending along the length of the wire 12 along the inner surface 24 thereof to define an inner longitudinal groove 40. The longitudinal grooves 30, 32, 36 and 40 cooperate with the shape of the exterior of the wire 12 to define corner projections 42 against which torquing forces may be applied. By this structure, the orthodontic wire 10 exhibits improved flexibility about an axis "O" oriented orthogonally relative to the longitudinal axis "L" when moment forces "M" are applied about the orthogonal axis "O" as shown in FIG. 3. Further, the orthodontic wire 10 retains the ability to impart torquing or torsional forces "T" about the longitudinal axis "L" as further shown in FIG. 3. Thus, the orthodontic wire 10 according to the present invention provides the flexibility of conventionally known round wires, while retaining the torquing ability of conventionally known square or rectangular wires.

Although not specifically illustrated, it is contemplated that the tooth bracket 14 through which the wire 12 extends may include a correspondingly shaped aperture extending therethrough which conforms to the grooves 30, 32, 36, and 40 of the wire. More specifically, the aperture extending through the tooth bracket 14 may be substantially rectangularly shaped so as to accommodate the upper surface 18, the lower surface 20, the outer surface 22, and the inner surface 24, and include correspondingly positioned interior projections which extend into the grooves 30, 32, 36, and 40, with the interior projections being closely shaped so as to completely fill each of the grooves.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A orthodontic wire comprising:

a length of wire for use in the construction of an orthodontics structure wherein said wire extends through a tooth bracket secured to an individual tooth within a patient's mouth, said wire having an upper surface spaced from and parallel to a lower surface, and an outer surface spaced from and parallel to an inner surface;

said wire being symmetrically oriented about a longitudinal axis and having an upper longitudinal cutout extending along said upper surface of said wire and parallel to said longitudinal axis, and a lower longitudinal cutout extending along said lower surface of said wire and parallel to said longitudinal axis, wherein said upper longitudinal cutout defines an upper longitudinal groove, and said lower longitudinal cutout defines a lower longitudinal groove;

said wire further having an outer longitudinal cutout extending along said outer surface of said wire and parallel to said longitudinal axis, and an inner longitudinal cutout extending along said inner surface of said wire and parallel to said longitudinal axis, wherein said outer longitudinal cutout defines an outer longitudinal groove, and said inner longitudinal cutout defines an inner longitudinal groove;

wherein said longitudinal grooves cooperate with a shape of an exterior of the wire to define corner projections against which torquing forces can be applied to said wire.

2. The orthodontic wire of claim 1, wherein said upper and lower surfaces are oriented at orthogonal angles relative to said outer and inner surfaces.

3. The orthodontic wire of claim 2, wherein said upper surface and said lower surface are of a first transverse dimensional length, and said outer surface and said inner surface are of a second transverse dimensional length, wherein said first transverse dimensional length is substantially greater than said second transverse dimensional length.

* * * * *